United States Patent [19]

Ose et al.

[11] 4,357,325

[45] Nov. 2, 1982

[54] METHODS OF CONTROLLING PASTEURELLA INFECTIONS

[75] Inventors: Earl E. Ose, Greenfield; Herbert A. Kirst, Indianapolis, both of Ind.

[73] Assignee: Eli Lilly and Company, Indianapolis, Ind.

[21] Appl. No.: 255,576

[22] Filed: Apr. 20, 1981

[51] Int. Cl.³ .................... A61K 31/71; C07H 17/04
[52] U.S. Cl. .................. 424/180; 424/181; 536/7.1
[58] Field of Search .................. 424/180, 181

[56] References Cited

U.S. PATENT DOCUMENTS

| | | | |
|---|---|---|---|
| 3,178,341 | 4/1965 | Hamill et al. | 167/65 |
| 3,326,759 | 6/1967 | Hamill et al. | 167/65 |
| 3,344,024 | 9/1967 | Whaley et al. | 167/65 |
| 3,459,853 | 8/1969 | Gorman et al. | 424/121 |
| 3,769,273 | 10/1973 | Massey | 260/210 |
| 3,975,372 | 8/1976 | Ganguly et al. | 536/17 R |
| 4,092,473 | 5/1978 | Okamoto et al. | 536/17 R |
| 4,234,690 | 11/1980 | Weinstein et al. | 435/119 |
| 4,252,898 | 2/1981 | Nash et al. | 435/76 |
| 4,279,896 | 7/1981 | Ganguly et al. | 424/181 |

OTHER PUBLICATIONS

Ziv. "Chem. Abst.", vol. 94, 1981, P41,975(f).
Ziv. "Chem. Abst.", vol. 94, 1981, P24,856(a).
K. Fujisawa et al., "Studies on Cirramycin $A_1$. II Biological Activity of Cirramycin $A_1$," *J. Antibiotics 22(2)*, 65–70 (1969).
H. Tsukiura et al., "Studies on Cirramycin $A_1$, IV Derivatives of Cirramycin $A_1$," *J. Antibiotics 22(3)*, 100–105 (1969).
T. Furumai et al., "Macrolide Antibiotics M-4365 Produced by Micromonospora. I. Taxonomy, Production, Isolation, Characterization and Properties," *J. Antibiotics 30*, 443–449 (1977).
T. Yamaguchi et al., "Macrolide Antibiotics M-4365 Produced by Micro-monospora III. In Vitro Antimicrobial Activity of Antibiotic M-4365 $G_2$ (De-epoxy Rosamicin)", *J. Antibiotics 31*, 433–440 (1978).

*Primary Examiner*—Johnnie R. Brown
*Attorney, Agent, or Firm*—Nancy J. Harrison; Arthur R. Whale

[57] ABSTRACT

Methods of controlling Pasteurella infections are provided which comprise administering to an infected or susceptible warm-blooded aninal an effective amount of a composition comprising (1) a suitable pharmaceutical vehicle and (2) a compound selected from the group consisting of desmycosin, lactenocin, cirramycin $A_1$, 23-deoxy-5-0-mycaminosyltylonolide, antibiotic M-4365 $G_2$, 9-dihydrodesmycosin, 9-dihydrolactenocin, 20-dihydrodesmycosin, 20-dihydrolactenocin, rosaramicin, and the pharmaceutically acceptable acid addition salts of these compounds.

24 Claims, No Drawings

METHODS OF CONTROLLING PASTEURELLA INFECTIONS

SUMMARY OF THE INVENTION

This invention relates to methods of controlling Pasteurella infections. In particular, this invention relates to methods of controlling Pasteurella infections which comprise administering to an infected or susceptible warm-blooded animal a compound selected from the group consisting of desmycosin, lactenocin, cirramycin $A_1$, 23-deoxy-5-O-mycaminosyltylonolide (DOMT), antibiotic M-4365 $G_2$ (repromicin), 9-dihydrodesmycosin, 9-dihydrolactenocin, 20-dihydrodesmycosin, 20-dihydrolactenocin, rosaramicin (rosamicin; M4365 $A_2$; juvenimicin $A_3$), and the pharmaceutically acceptable acid addition salts of these compounds.

Pasteurella infections cause serious economic losses in animals. Pasteurellosis, which is a respiratory disease in sheep, cattle and pigs, and fowl cholera are examples of severe diseases in which Pasteurella species are either the primary, or important secondary, etiological agents. P. multocida and P. haemolytica are the agents implicated in these diseases.

DETAILED DESCRIPTION OF THE INVENTION

We have discovered that a certain group of macrolide antibiotics exhibit unexpectedly high antibacterial activity against certain gram-negative bacteria, i.e. Pasteurella species. More particularly, we have discovered that these compounds are effective in vivo as well as in vitro against Pasteurella species such as P. multocida and P. haemolytica.

The structures of the macrolide compounds which are useful in the method of this invention are shown in formula 1 and Table 1:

TABLE I

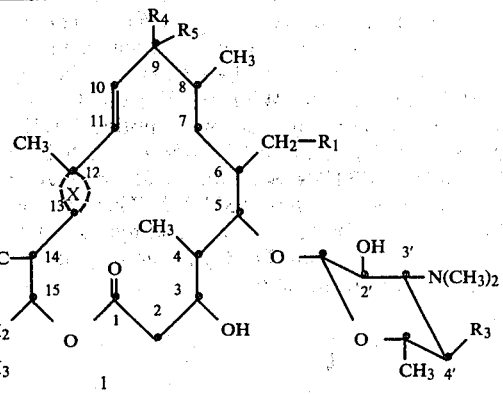

| Compound | X | $R_1$ | $R_2$ | $R_3$ | $R_4,R_5$ | $R_7$ |
|---|---|---|---|---|---|---|
| Desmycosin | db[a] | —CHO | $R_6$[c] | —OH | =O | —CH$_3$ |
| Lactenocin | db | —CHO | $R_6$ | —OH | =O | —H |
| 23-Deoxy-5-O—mycaminosyltylonolide | db | —CHO | —H | —OH | =O | — |
| Rosaramicin | epoxy[b] | —CHO | —H | —H | =O | — |
| M-4365 $G_2$ | db | —CHO | —H | —H | =O | — |
| Cirramycin $A_1$ | epoxy | —CHO | —H | —OH | =O | — |
| 20-Dihydrodesmycosin | db | —CH$_2$OH | $R_6$ | —OH | =O | —CH$_3$ |
| 20-Dihydrolactenocin | db | —CH$_2$OH | $R_6$ | —OH | =O | —H |
| 9-Dihydrodesmycosin | db | —CHO | $R_6$ | —OH | H,OH | —CH$_3$ |
| 9-Dihydrolactenocin | db | —CHO | $R_6$ | —OH | H,OH | —H |

[a] double bond ( C=C )

[b] (epoxy structure)

[c] 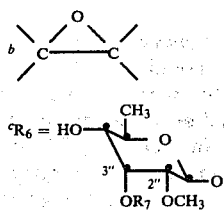

The compounds used in the methods of this invention are either known antibiotics or are readily prepared from known antibiotics. The preparation of desmycosin is described by R. L. Hamill et al. in U.S. Pat. No. 3,178,341, issued Apr. 13, 1965. The preparation of lactenocin is described by R. L. Hamill et al. in U.S. Pat. No. 3,326,759, issued June 20, 1967. Cirramycin $A_1$ is prepared as described by H. Koshiyama et al., J. Antibiotics Ser. A16, 59–66 (1963) and S. Nash et al. in U.S. Pat. No. 4,252,898, issued Feb. 24, 1981. Antibiotic M-4365 $G_2$ (repromicin) can be prepared as described by T. Furumai et al. in J. Antibiotics 30, 443–449 (1977) or as described by A. K. Ganguly in U.S. Pat. No. 3,975,372, issued Aug. 17, 1976. The preparation of 9-dihydrodesmycosin (dihydrodesmycosin) is described by E. H. Massey in U.S. Pat. No. 3,769,273, issued Oct. 30, 1973. 9-Dihydrolactenocin is prepared in an analogous manner. Rosaramicin can be prepared as described by M. J. Weinstein et al. in U.S. Pat. No. 4,234,690, issued Nov. 18, 1980.

20-Dihydrodesmycosin and 20-dihydrolactenocin can be prepared by chemical reduction using known procedures such as, for example, treatment with an approximately stoichiometric amount of sodium borohydride in an alcoholic solvent.

DOMT is identical to depoxyciramycin $A_1$ (de-epoxycirramycin $A_1$). The preparation and activity of depoxycirramycin $A_1$ are described by H. Tsukiura et al. in *J. Antibiotics* 22 (3) 89–99, and 100–105 (1969). Tsukiura et al. prepare deoxycirramycin $A_1$ by treating cirramycin $A_1$ with potassium iodide in acetic acid.

Another method of preparing DOMT is described by Richard H. Baltz, Gene M. Wild, and Eugene T. Seno in their copending application entitled DE(-MYCINOSYLOXY) TYLOSIN AND PROCESS FOR ITS PRODUCTION, Ser. No. 156,855, filed June 12, 1980, now U.S. Pat. No. 4,321,362. This method comprises preparing DOMT by mild acid hydrolysis of 23-de(mycinosyloxy)tylosin (DMOT). The structure of DMOT is shown in formula 2:

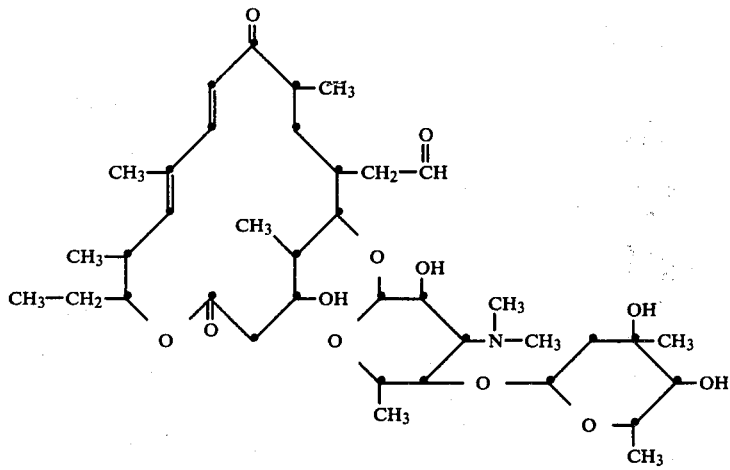

2

DMOT is prepared by fermentation of *Streptomyces fradiae* NRRL 12171 under submerged aerobic conditions until a substantial level of antibiotic activity is produced. DMOT can be extracted from basified broth filtrate with polar organic solvents and can be further purified by extraction, chromatography, and/or crystallization.

The DMOT-producing strain of *Streptomyces fradiae* has been deposited and made part of the stock culture collection of the Northern Regional Research Center, Agricultral Research, North Central Region, 1815 North University Street, Peoria, Ill., 61604, from which it is available to the public under the accession number NRRL 12171.

DOMT is prepared from DMOT by mild acid hydrolysis. Appropriate solutions having a pH of about four or below can be used to accomplish the hydrolysis. Temperatures of about 20° to about 100° C. can be used in this method. The reaction time needed to carry out the hydrolysis varies, depending upon the pH of the reaction mixture and the temperature used. At higher pH levels the reaction rate is slower, and at higher temperatures the reaction rate is faster. The reaction is carried out by treating DMOT with a mild acid solution for a time sufficient to effect removal of the mycarosyl group to give DOMT.

Alternatively, and sometimes preferably, DOMT can be prepared by treating DMOT in the fermentation broth in which it is produced, using mild acidic conditions as above described for a time sufficient to convert the DMOT to DOMT. DOMT thus prepared can be isolated from the fermentation using techniques known in the art.

In carrying out the method of this invention, a specified compound of formula 1 or a pharmaceutically acceptable acid addition salt thereof is administered parenterally to an infected or susceptible warm-blooded animal. The dose used to control Pasteurella infections will vary with the compound, the severity of the infection, and the age, weight, and condition of the animal. The total dose required for several days protection will generally, however, be in the range of from about 10 to about 400 mg/kg and preferably will be in the range of from about 25 to about 350 mg/kg. Protection for up to about seven days can be provided by a single injection; the length of protection will depend upon the dose given. The total dose can also be divided into smaller doses given at intervals, such as once daily for four to seven days. Obviously, other suitable dosage regimens can be constructed.

The compounds of this invention may be formulated for parenteral administration by methods recognized in the veterinary pharmaceutical art. Effective injectable compositions containing these compounds may be in either suspension or solution form. In the preparation of suitable formulations it will be recognized that, in general, the water solubility of the acid addition salts is greater than that of the corresponding free bases. Similarly, the free bases are more soluble in dilute acids or in acidic solutions than in neutral or basic solutions.

In the solution form a compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions employ a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antifoams, sorbitol, and sugars can be useful suspending agents.

The compounds of this invention exhibit unexpectedly high antibacterial activity against *Pasteurella* species. For example, representative compounds were tested against avian, bovine and porcine *Pasteurella* species, using the conventional broth-dilution assay. The *P. haemolytica* strains are bovine strains; the *P. multocida* strains are avian, bovine and porcine strains. The minimal inhibitory concentrations (MIC's) of representative compounds against these species are summarized in Table II.

TABLE II

MIC Of Compounds Against Pasteurella Species

| | MIC Values (mcg/ml) | | | | | | | |
|---|---|---|---|---|---|---|---|---|
| | *P. haemolytica* Strains | | | *P. multocida* Strains | | | | |
| Compound | 23A | 41D | 23C | 22A | 40G | 68C | 17E | 60A |
| Desmycosin | 25 | 25 | 25 | 12.5 | 25 | 6.25 | 12.5 | 12.5 |
| Lactenocin | 25 | 50 | 25 | 12.5 | 25 | 6.25 | 12.5 | 6.25 |
| Rosaramicin | 1.56 | 1.56 | 12.5 | 1.56 | 1.56 | ≦0.78 | ≦0.78 | ≦0.78 |
| Cirramycin A$_1$ | 3.12 | 3.12 | 3.12 | 3.12 | 3.12 | 1.56 | 1.56 | ≦0.78 |
| DOMT | 3.12 | 6.75 | 3.12 | 1.56 | 3.12 | ≦0.78 | 1.56 | ≦0.78 |
| 20-Dihydrodesmycosin | 50 | 50 | 50 | 25 | 50 | 6.25 | 25 | 25 |
| 9-Dihydrodesmycosin | 25 | 25 | 25 | 12.5 | 12.5 | 12.5 | 12.5 | 12.5 |

Examples 1 and 2 illustrate the useful in vivo activity of the compounds of this invention.

EXAMPLE 1

Treatment of Pasteurellosis in Chicks

Representative compounds were evaluated in groups of ten one-day-old chicks at the specified dosage of subcutaneous injection given one and four hours post challenge of the chicks with *Pasteurella multocida* (0.1 ml of a 20-hour tryptose broth culture of an avian *P. multocida* given subcutaneously). The compounds (as free bases) were administered in an aqueous propylene glycol solution; non-medicated water and feed were provided to the animals ad libitum. The chicks were observed for the following five days. Results of these tests are summarized in Table III.

TABLE III

Treatment of Pasteurella Infections in Chicks

| Compound | Dosage (mg/kg × 2) | Deaths in Treated Chicks/ Deaths in Infected Nonmedicated Controls[a] |
|---|---|---|
| Desmycosin | 30 | 0/10, 0/10[b] |
| Lactenocin | 30 | 0/10, 0/10[b] |
| 9-Dihydrodesmycosin | 30 | 3/10, 0/10[b] |
| DOMT | 30 | 1/9, 1/10[b] |
| 20-Dihydrodesmycosin | 30 | 0/10, 0/10[b] |
| Rosaramicin | 60 | 2/8 |
| Rosaramicin | 30 | 5/8 |

[a] Ten chicks in each treatment group
[b] Two experiments

EXAMPLE 2

Treatment of Pasteurellosis in Mice

Cirramycin A$_1$ and rosaramicin were evaluated in mice by subcutaneous injection given one and four hours post challenge of the mice with *Pasteurella multocida* (0.1 ml of a $10^{-5}$ dilution of a tryptose broth culture of a bovine isolate). Mortality was evaluated for the following seven days. The results are summarized in Table IV.

TABLE IV

Treatment of Pasteurellosis in Mice with Cirramycin A$_1$ and Rosaramicin

| Compound | Dosage (mg/kg × 2) | Test | Replicate | No. Died/ No. Treated |
|---|---|---|---|---|
| Cirramycin A$_1$ | 50 | A | 1 | 1/5 |
| | | | 2 | 2/5 |
| | | B | 1 | 1/5 |
| | | | 2 | 0/5 |
| Rosaramicin | 50 | A | 1 | 0/5 |
| | | | 2 | 0/5 |
| | | B | 1 | 0/5 |
| | | | 2 | 3/5 |
| Nonmedicated Controls | | A | 1 | 1/5 |
| | | | 2 | 5/5 |
| | | B | 1 | 3/5 |
| | | | 2 | 4/5 |

EXAMPLE 3

Injectable Formulations (A) Desmycosin base is added to propylene glycol. Water and benzyl alcohol are added so that the solution contains 50% (by volume) propylene glycol, 4% (by volume) benzyl alcohol and 200 mg/ml of desmycosin base.

(B) A desmycosin solution is prepared as described in Section A except that the solution contains 50 mg/ml of desmycosin base.

(C) A desmycosin solution is prepared as described in Section A except that the solution contains 500 mg/ml of desmycosin tartrate.

(D) A solution prepared as described in Section A but using lactenocin.

(E) A solution prepared as described in Section A but using 20-dihydrodesmycosin.

(F) A solution prepared as described in Section A but using 23-deoxy-5-O-mycaminosyltylonolide (DOMT).

(G) A solution prepared as described in Section A but using 9-dihydrodesmycosin.

(H) A solution prepared as described in Section C but using rosaramicin.

(I) A desmycosin suspension is prepared by adding finely ground desmycosin to carboxymethylcellulose with thorough mixing so that each ml of finished suspension contains 200 mg of desmycosin.

EXAMPLE 4

Preparation of DOMT from DMOT

A. Shake-flask Fermentation of DMOT

A lyophilized pellet of *Streptomyces fradiae* NRRL 12171 is dispersed in 1–2 ml of sterilized water. A portion of this solution (0.5 ml) is used to inoculate a vegetative medium (150 ml) having the following composition:

| Ingredient | Amount (%) |
| --- | --- |
| Corn steep liquor | 1.0 |
| Yeast extract | 0.5 |
| Soybean grits | 0.5 |
| CaCO$_3$ | 0.3 |
| Soybean oil (crude) | 0.45 |
| Deionized water | 97.25 |

Alternatively, a vegetative culture of *S. fradiae* NRRL 12171, preserved in 1-ml volumes in liquid nitrogen, is rapidly thawed and used to inoculate the vegetative medium. The inoculated vegetative medium is incubated in a 500-ml Erlenmeyer flask at 29° C. for about 48 hours on a closed-box shaker at 300 rpm.

This incubated vegetative medium (0.5 ml) is used to inoculate 7 ml of a production medium having the following composition:

| Ingredient | Amount (%) |
| --- | --- |
| Beet molasses | 2.0 |
| Corn meal | 1.5 |
| Fish meal | 0.9 |
| Corn gluten | 0.9 |
| NaCl | 0.1 |
| (NH$_4$)$_2$HPO$_4$ | 0.04 |
| CaCO$_3$ | 0.2 |
| Soybean oil (crude) | 3.0 |
| Deionized water | 91.36 |

The inoculated fermentation medium is incubated in a 50-ml bottle at 29° C. for about 6 days on a closed-box shaker at 300 rpm.

B. Tank Fermentation of DMOT

In order to provide a larger volume of inoculum, 60 ml of incubated vegetative medium, prepared in a manner similar to that described in section A, is used to inoculate 38 L of a second-stage vegetative growth medium having the following composition:

| Ingredient | Amount (%) |
| --- | --- |
| Corn steep liquor | 1.0 |
| Soybean oil meal | 0.5 |
| Yeast extract | 0.5 |
| CaCO$_3$ | 0.3 |
| Soybean oil (crude) | 0.5 |
| Lecithin (crude) | 0.015 |
| Water | 97.185 |

Adjust pH to 8.5 with 50% NaOH solution.

This second-stage vegetative medium is incubated in a 68-liter tank for about 47 hours at 29° C.

Incubated second-stage medium (4 L) thus prepared is used to inoculate 40 liters of sterile production medium having the following composition:

| Ingredient | Amount (%) |
| --- | --- |
| Fish meal | 0.9188 |
| Corn meal | 1.575 |
| Corn gluten | 0.9188 |
| CaCO$_3$ | 0.210 |
| NaCl | 0.105 |
| (NH$_4$)$_2$HPO$_4$ | 0.042 |
| Beet molasses | 2.10 |
| Soybean oil (crude) | 3.15 |
| Lecithin | 0.0945 |
| Water | 90.8859 |

Adjust pH to 7.2 with 50% NaOH solution.

The inoculated production medium is allowed to ferment in a 68-liter tank for about 5 days at a temperature of 28° C. The fermentation medium is aerated with sterile air to keep the dissolved oxygen level between about 30% and 50% and is stirred with conventional agitators at about 300 rpm.

C. Isolation of DMOT

Fermentation broth, obtained as described in Section B, and having a pH of 7.2, is filtered using a filter aid. Ethyl acetate (400 ml) is added to the filtrate (1450 ml). The pH of the solution is adjusted to 9.1 by the addition of sodium hydroxide. The solution is stirred 10 minutes, and the ethyl acetate is separated (filtering through a filter aid to clear any emulsion which forms). The filtrate is again extracted with ethyl acetate (200 ml). Water (200 ml) is added to the combined ethyl acetate extracts; the pH of this solution is adjusted to 4.1 with phosphoric acid. After extraction, the aqueous phase is separated, and the organic phase is discarded. The aqueous phase is adjusted to pH 9.1 with sodium hydroxide and then concentrated to a volume of about 100 ml under vacuum. An amorphous precipitate forms. After permitting the precipitate to stand overnight, it is separated by filtration. The precipitate is dissolved in acetone (20 ml); water (75 ml) is added. The solution is concentrated under vacuum to remove acetone. The precipitate which forms is separated by filtration and washed with water to give about 500 mg of DMOT (2). An additional 260 mg is obtained in a similar manner from the filtrate.

D. Preparation of DOMT

DMOT (11 g), prepared as described in Section C, is dissolved in a dilute hydrochloric acid solution (final pH 1.8). The resulting solution is allowed to stand for 24 hours at room temperature and then is adjusted to pH 9.0 by addition of sodium hydroxide. This basic solution is extracted with chloroform. The chloroform extract is evaporated under vacuum to give 9.65 g of DOMT.

EXAMPLE 5

Alternative Preparation of DOMT

DOMT is prepared from DMOT by treating DMOT in the fermentation broth in which it is produced with mild acid as described in Section D of Example 4. Isolation of DOMT is accomplished by a procedure similar to that described for DMOT in Section C of Example 4.

We claim:

1. A method for controlling Pasteurella infections which comprises administering to an infected or susceptible warm-blooded animal an effective amount of a composition comprising (1) a suitable pharmaceutical vehicle and (2) a compound selected from the group consisting of desmycosin, lactenocin, cirramycin $A_1$, 23-deoxy-5-O-mycaminosyltylonolide, antibiotic M-4365 $G_2$, 9-dihydrodesmycosin, 9-dihydrolactenocin, 20-dihydrodesmycosin, 20-dihydrolactenocin, rosaramicin, and the pharmaceutically acceptable acid addition salts of these compounds.

2. The method of claim 1 wherein the compound is desmycosin or a pharmaceutically acceptable acid addition salt of desmycosin.

3. The method of claim 2 wherein the compound is desmycosin.

4. The method of claim 2 wherein the compound is desmycosin tartrate or desmycosin phosphate.

5. The method of claim 1 wherein the compound is lactenocin or a pharmaceutically acceptable acid addition salt of lactenocin.

6. The method of claim 5 wherein the compound is lactenocin.

7. The method of claim 1 wherein the compound is cirramycin $A_1$ or a pharmaceutically acceptable acid addition salt of cirramycin $A_1$.

8. The method of claim 7 wherein the compound is cirramycin $A_1$.

9. The method of claim 1 wherein the compound is 23-deoxy-5-O-mycaminosyltylonolide or a pharmaceutically acceptable acid addition salt thereof.

10. The method of claim 9 wherein the compound is 23-deoxy-5-O-mycaminosyltylonolide.

11. The method of claim 1 wherein the compound is antibiotic M-4365 $G_2$ or a pharmaceutically acceptable acid addition salt thereof.

12. The method of claim 11 wherein the compound is antibiotic M-4365 $G_2$.

13. The method of claim 1 wherein the compound is 9-dihydrodesmycosin or a pharmaceutically acceptable acid addition salt thereof.

14. The method of claim 13 wherein the compound is 9-dihydrodesmycosin.

15. The method of claim 1 wherein the compound is 20-dihydrodesmycosin or a pharmaceutically acceptable acid addition salt thereof.

16. The method of claim 15 wherein the compound is 20-dihydrodesmycosin.

17. The method of claim 1 wherein the compound is 20-dihydrolactenocin or a pharmaceutically acceptable acid addition salt thereof.

18. The method of claim 17 wherein the compound is 20-dihydrolactenocin.

19. The method of claim 1 wherein the compound is rosaramicin or a pharmaceutically acceptable acid addition salt thereof.

20. The method of claim 19 wherein the compound is rosaramicin.

21. The method of claim 1 wherein the compound is 9-dihydrolactenocin or a pharmaceutically acceptable acid addition salt thereof.

22. The method of claim 21 wherein the compound is 9-dihydrolactenocin.

23. The method of claim 1, 2, 5, 7, 9, 11, 13, 15, 17, 19 or 21 wherein the composition is administered as a single injection.

24. The method of claim 1, 2, 5, 7, 9, 11, 13, 15, 17, 19 or 21 wherein divided doses of the composition are administered.

* * * * *